(12) United States Patent
Kosonen et al.

(10) Patent No.: US 11,511,015 B2
(45) Date of Patent: Nov. 29, 2022

(54) MEDICAL MULTI-LAYER PRODUCT COMPRISING NANOFIBRILLAR CELLULOSE AND METHOD FOR PREPARING THEREOF

(71) Applicant: UPM-KYMMENE CORPORATION, Helsinki (FI)

(72) Inventors: Mika Kosonen, Lappeenranta (FI); Kari Luukko, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 1185 days.

(21) Appl. No.: 16/065,233

(22) PCT Filed: Dec. 30, 2016

(86) PCT No.: PCT/FI2016/050938
§ 371 (c)(1),
(2) Date: Jun. 22, 2018

(87) PCT Pub. No.: WO2017/115018
PCT Pub. Date: Jul. 6, 2017

(65) Prior Publication Data
US 2021/0205490 A1   Jul. 8, 2021

(30) Foreign Application Priority Data
Dec. 31, 2015   (EP) .................................... 15397547

(51) Int. Cl.
*A61L 15/22*      (2006.01)
*A61F 13/00*     (2006.01)
(Continued)

(52) U.S. Cl.
CPC ...... *A61L 15/225* (2013.01); *A61F 13/00012* (2013.01); *A61F 13/00017* (2013.01);
(Continued)

(58) Field of Classification Search
CPC .......... A61F 13/00012; A61F 13/00017; A61F 13/00029; A61F 13/00042;
(Continued)

(56) References Cited

U.S. PATENT DOCUMENTS 4,638,796 A  *  1/1987  Sims ....................... A61F 13/10
                                                          602/45
6,202,946 B1     3/2001  Virtanen
(Continued)

FOREIGN PATENT DOCUMENTS

CN     104906620 A     9/2015
EP      2781652 A1     9/2014
(Continued)

OTHER PUBLICATIONS

European Search Report for European Application No. 15397547.9, International Filing Date Dec. 31, 2015, dated Jul. 7, 2016, 6 pages.
(Continued)

*Primary Examiner* — Susan S Su
(74) *Attorney, Agent, or Firm* — Cantor Colburn LLP

(57) ABSTRACT

The present application provides a medical multi-layer product comprising a layer comprising nanofibrillar cellulose, and a layer of gauze. The present application also provides a medical product comprising the medical multi-layer product, and a cosmetic product comprising the medical multi-layer product. The present application also provides a method for preparing a medical multi-layer product, the method comprising providing a filter, providing a dispersion comprising nanofibrillar cellulose, providing a gauze, applying the dispersion onto the filter, applying the gauze onto the dispersion, and dewatering the structure through the filter to obtain the medical multi-layer product.

33 Claims, 1 Drawing Sheet

(51) Int. Cl.
    *A61L 15/28* (2006.01)
    *A61L 15/40* (2006.01)
    *A61L 15/44* (2006.01)

(52) U.S. Cl.
    CPC .. *A61F 13/00029* (2013.01); *A61F 13/00042* (2013.01); *A61F 13/00987* (2013.01); *A61L 15/28* (2013.01); *A61L 15/40* (2013.01); *A61L 15/44* (2013.01); *A61L 2400/12* (2013.01)

(58) Field of Classification Search
    CPC .. A61F 13/00987; A61L 15/225; A61L 15/28; A61L 15/40; A61L 15/44; A61L 2400/12; A61L 15/60; A61L 27/20; A61L 27/52; A61L 27/60; A61L 15/22; B82Y 5/00
    See application file for complete search history.

(56) References Cited

U.S. PATENT DOCUMENTS

| | | | |
|---|---|---|---|
| 2007/0053960 A1* | 3/2007 | Brown, Jr. | ............ A61L 15/16 514/9.2 |
| 2015/0367024 A1* | 12/2015 | Laukkanen | ......... A61L 26/0023 424/444 |
| 2018/0327971 A1 | 11/2018 | Gane et al. | |

FOREIGN PATENT DOCUMENTS

| | | |
|---|---|---|
| RU | 2448738 C2 | 4/2012 |
| RU | 135921 U1 | 12/2013 |
| WO | 2005084650 A1 | 9/2005 |
| WO | 2007056066 A2 | 5/2007 |
| WO | 2011116069 A1 | 9/2011 |
| WO | 2014071523 A1 | 5/2014 |
| WO | 2014128354 A1 | 8/2014 |
| WO | 2015011337 A1 | 1/2015 |
| WO | 2015101711 A1 | 7/2015 |
| WO | 2015101712 A1 | 7/2015 |

OTHER PUBLICATIONS

International Preliminary Report on Patentability for International Application No. PCT/FI2016/050938, International Filing Date Dec. 30, 2016, dated Dec. 18, 2017, 6 pages.

International Search Report for International Application No. PCT/FI2016/050938, International Filing Date Dec. 30, 2016, dated Feb. 27, 2017, 5 pages.

Written Opinion for International Application No. PCT/FI2016/050938, International Filing Date Dec. 30, 2016, dated Feb. 27, 2017, 5 pages.

* cited by examiner

MEDICAL MULTI-LAYER PRODUCT COMPRISING NANOFIBRILLAR CELLULOSE AND METHOD FOR PREPARING THEREOF

CROSS-REFERENCE TO RELATED APPLICATIONS

This application is a National Stage application of PCT/FI2016/050938, filed Dec. 30, 2016, which claims the benefit of European Application No. 15397547.9, filed Dec. 31, 2015, both of which are incorporated by reference herein in their entirety.

FIELD OF THE APPLICATION

The application relates to a nanofibrillar cellulose membrane and to a multi-layer product comprising nanofibrillar cellulose. The present application also relates to a method for preparing a membrane from nanofibrillar cellulose and to a method for preparing a multi-layer product.

BACKGROUND

Nanofibrillar cellulose refers to isolated cellulose fibrils or fibril bundles derived from cellulose raw material. Nanofibrillar cellulose is based on a natural polymer that is abundant in nature. Nanofibrillar cellulose has a capability of forming viscous gel in water (hydrogel).

Nanofibrillar cellulose production techniques are based on grinding (or homogenization) of aqueous dispersion of pulp fibers. The concentration of nanofibrillar cellulose in dispersions is typically very low, usually around 0.3-5%. After the grinding or homogenization process, the obtained nanofibrillar cellulose material is a dilute viscoelastic hydrogel.

There is also interest in making structural products from nanofibrillar cellulose by removing water to the extent that the product exists as a self-supporting structure in form of a membrane.

SUMMARY

One embodiment provides a medical multi-layer product comprising
 a layer comprising nanofibrillar cellulose, and
 a layer of gauze.

One embodiment provides a medical multi-layer product comprising
 a first layer comprising nanofibrillar cellulose,
 a layer of gauze, and
 a second layer comprising nanofibrillar cellulose.

One embodiment provides a medical product, such as a dressing or a patch, comprising said medical multi-layer product.

One embodiment provides the medical multi-layer product for use for covering and/or treating skin wounds or other damages.

One embodiment provides a cosmetic product, such as a dressing or a patch, comprising said medical multi-layer product.

One embodiment provides a method for preparing a medical multi-layer product, said method comprising
 providing a layer comprising nanofibrillar cellulose,
 providing a layer of gauze, and
 laminating the layer comprising nanofibrillar cellulose and the layer of gauze to obtain the medical multi-layer product.

A method for preparing a medical multi-layer product, the method comprising
 providing a filter,
 providing a dispersion comprising nanofibrillar cellulose,
 providing a gauze,
 applying the dispersion onto the filter,
 applying the gauze onto the dispersion, and
 dewatering the structure through the filter to obtain the medical multi-layer product.

The main embodiments are characterized in the independent claims. Various embodiments are disclosed in the dependent claims. The embodiments recited in dependent claims and in the description are mutually freely combinable unless otherwise explicitly stated.

The medical structure of the embodiments provides enhanced mechanical strength and other properties, such as high tear strength (tear resistance), especially at moist conditions. By adding a supporting and reinforcing structure, such as a dressing fabric, i.e. the gauze, to a membrane a multi-layer structure, for example a two layer or a three layer structure can be formed. The fabric creates a continuous supporting network and the strength of the network is not significantly affected by moist conditions. By producing a three layer structure the fabric may stay fixed inside the structure and risk of fabric separation from a membrane is decreased.

Tear strength of a membrane or the structure may be further enhanced by adding an amount of non-nanofibrillar cellulose in a membrane comprising nanofibrillar cellulose. Even a relative small amount of non-nanofibrillar cellulose in the membrane effectively enhances the tear strength.

In the preparation process the enhanced tear strength also facilitates the removal of the dried membrane from a support, such as a filter fabric, as the membrane is not prone to tearing.

Certain advantageous properties of the medical multi-layer products include flexibility, elasticity and remouldability. If the nanofibrillar layer contains moisture, it may also show good permeability. These properties are useful for example when the structure is used as a dressing for healing wounds, or in other medical applications, such as for delivering therapeutic or cosmetic agents.

Flexibility is a feature which is desired in many applications, such as in medical applications. For example flexible patches and dressings comprising nanofibrillar cellulose are useful for applying onto skin, for example for covering wounds and other damages or injuries, such as burns.

The flexibility or elasticity (elongation) of the structure can also be affected in small scale with the choice of the gauze. Also a relative small amount of non-nanofibrillar cellulose in the membrane may enhance the flexibility.

The medical multi-layer products of the embodiments also provide high absorption capacity and absorption speed, which properties are desired in medical applications such as wound healing and the like. Large membranes may be prepared which may be used for covering large areas.

The multi-layer products described herein are useful in medical applications, wherein the materials comprising nanofibrillar cellulose are in contact with living tissue. It was discovered that nanofibrillar cellulose provides unusual properties when it is applied for example onto skin. The products containing nanofibrillar cellulose as described herein are highly biocompatible with the living tissue and provide several advantageous effects. Without binding to any specific theory, it is believed that a layer comprising nanofibrillar cellulose provides a very high surface area, which, when applied against a skin or other tissue, absorbs water from the skin and forms special conditions between the tissue and the layer comprising nanofibrillar cellulose. The multi-layer product may be also be moistened to enhance the effect. Further, a thin gel layer will be formed onto the surface of the layer comprising nanofibrillar cellulose, and water molecules are present between this gel layer and the skin. The free hydroxyl groups in the nanofibrillar cellulose facilitate formation of hydrogen bonds between the material and water molecules. This will enhance contact with the skin and enable migration of fluids and/or agents from the skin to the multi-layer product, or from the multi-layer product to the skin.

When the multi-layer products are used for covering wounds or other damages or injuries, for example as plasters, dressings, medical patches or parts of plasters, patches or dressings, several effects are provided. The usability of the products is good as the product may be applied and removed easily without being damaged, for example torn. When used for covering wounds the material of the product acts as an artificial skin, which protects the wound and will come loose when the wound heals. The product will not attach to a damaged skin in such irreversible way as conventional materials, which are usually very difficult to remove without damaging the healed area. The conditions between the product and the skin facilitate the healing of a damaged area.

The medical multi-layer products of the embodiments are especially advantageous in the treatment of grafts, such as skin graft. The multi-layer product may be used for covering the graft area and it acts as a protective layer. As the graft heals, the membrane forms a scab-like structure, which promotes the healing.

The multi-layer products may be used for controllably and effectively delivering agents, such as therapeutic or cosmetic agents, to a patient or user.

BRIEF DESCRIPTION OF THE DRAWINGS

The embodiments will be explained in the following with reference to the appended drawings, where.

DETAILED DESCRIPTION

Figure 1:
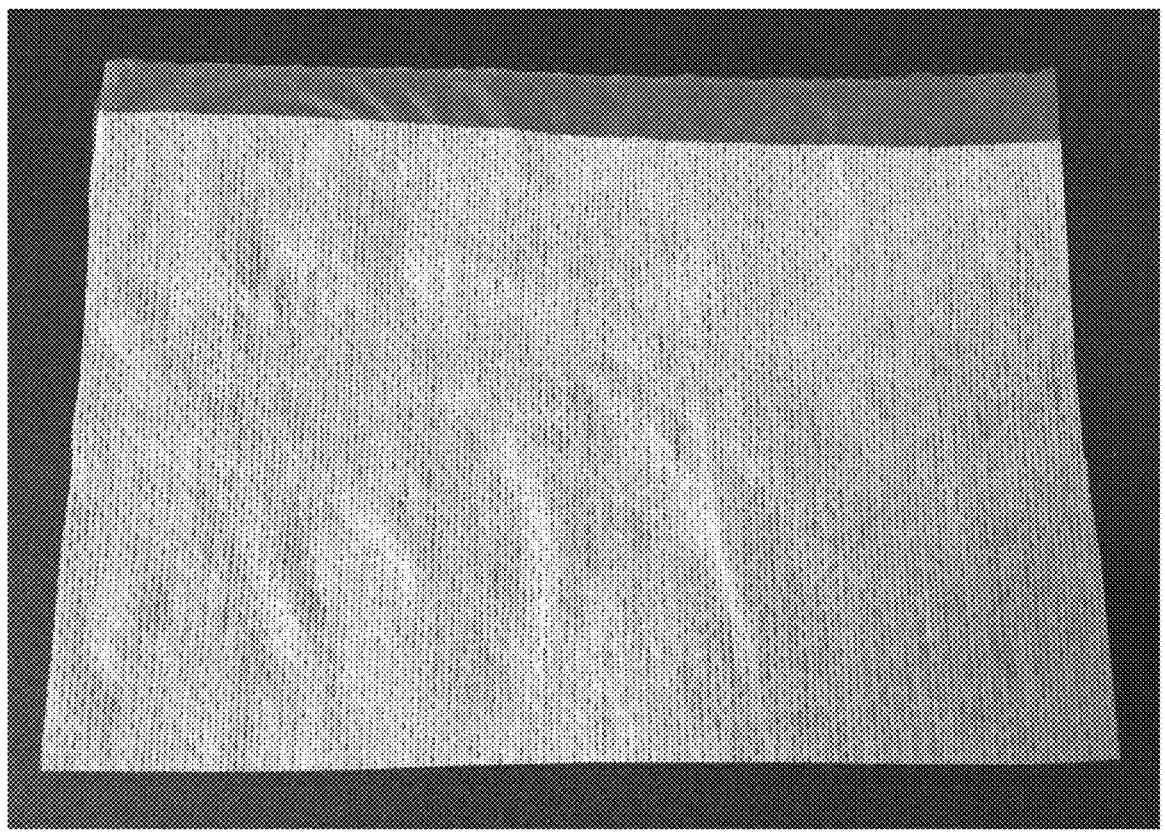
FIG. 1 shows an example of a product comprising three layers; a layer of gauze is between a first layer comprising nanofibrillar cellulose and a second layer comprising nanofibrillar cellulose. The layers of nanofibrillar cellulose overlap at the upper side of the image.

In this specification, percentage values, unless specifically indicated otherwise, are based on weight (w/w). If any numerical ranges are provided, the ranges include also the upper and lower values.

The embodiments provide at least one layer comprising nanofibrillar cellulose and optionally other ingredients, such as non-nanofibrillar pulp or therapeutic or cosmetic agents or other agents. One embodiment provides a layer comprising nanofibrillar cellulose and non-nanofibrillar pulp. The amount of the non-nanofibrillar pulp in the layer may be in the range of 0.1-60% (w/w), for example 0.1-50% (w/w), of total cellulose. The cellulose layer comprising nanofibrillar cellulose and optionally a portion of non-nanofibrillar pulp may be called herein also for example as a "layer", a "layer of membrane", a "membrane", a "layer comprising nanofibrillar cellulose" or a "membrane comprising nanofibrillar cellulose". Examples of such layers include the first layer comprising nanofibrillar cellulose and the second layer comprising nanofibrillar cellulose as described herein, or any further layers.

In general said layers or membranes may be prepared by providing a dispersion comprising nanofibrillar cellulose, and drying said dispersion on a support. The support may include a filter or a filter may be provided in addition to the support, wherein the dewatering is carried out through the filter, which retains the nanofibrillar cellulose but allows water to pass. As a result a layer comprising nanofibrillar cellulose is obtained as dried having a moisture content in the range of 0-10%, for example 1-10%. In general the moisture content may be affected by the ambient atmosphere and in many cases it is in the range of 5-7%.

The layers or membranes comprising nanofibrillar cellulose may be used in the multi-layered products described herein. In one embodiment the multi-layered products comprise at least a layer comprising nanofibrillar cellulose, and a layer of gauze.

The "medical multi-layer product" as used herein refers to a structure having at least two layers, and which may be used for example in medical applications. However, said multi-layered structures may be used in other suitable applications as well. In one embodiment the medical multi-layer product comprises two layers. In one embodiment the medical multi-layer product comprises three layers. The at least two layers are laminated or layered together to form a multi-layered product or structure, more particularly a laminated or layered multi-layered product or structure. The medical multi-layer product may contain further layers, which may be gauze layers, layers comprising nanofibrillar cellulose, or other layers such as reinforcing or covering/backing layers, such as plastic or fibrous layers.

The term "medical" refers to a product or use wherein the product is used or is suitable for medical purposes. A medical product may be sterilized, or it is sterilisable, for example by using temperature, pressure, moisture, chemicals, radiation or a combination thereof. The product may be for example autoclaved, or other methods using high temperature may be used, in which cases the product should tolerate high temperatures over 100° C., for example at least 121° C. or 134° C. A medical product may also be suitable for example for cosmetic purposes.

Starting Materials for Preparing a Layer Comprising Nanofibrillar Cellulose

One starting material comprises nanofibrillar cellulose, which comprises or consists of cellulose fibrils having diameter in the submicron range. It forms a self-assembled hydrogel network even at low concentrations. These gels of nanofibrillar cellulose are highly shear thinning and thixotrophic in nature.

One optional further starting material comprises non-nanofibrillar pulp. Such pulp is in general conventional or regular pulp or cellulose and it may be also called as macrofibrillar pulp or macrofibrillar cellulose. In one embodiment the non-nanofibrillar pulp is unrefined or moderately refined pulp, which may be characterized for example by pulp freeness.

Said two main starting materials may also be called as fractions, such as a nanofibrillar cellulose fraction and a non-nanofibrillar pulp fraction. The nanofibrillar cellulose fraction is usually the main fraction of the cellulosic material of the membrane, or the dispersion for preparing the membrane, for example comprising 80-99.9% (w/w) of the dry weight of total cellulose. However, in one embodiment the membrane does not contain any non-nanofibrillar pulp, i.e. the amount of non-nanofibrillar pulp is 0%. The non-nanofibrillar pulp is usually the minor fraction or portion of the cellulosic material of the membrane. In one embodiment the nanofibrillar cellulose membrane comprises an amount of non-nanofibrillar pulp in the range of 0.1-60% (w/w) of total cellulose, for example in the range of 0.1-50% (w/w), 0.1-40% (w/w), 0.1-30% (w/w), 0.1-20% (w/w), 0.1-10% (w/w), 0.5-10% (w/w), 1-10% (w/w), 0.5-5% (w/w), 1-5% (w/w), 0.5-3% (w/w) or 1-3% (w/w) of total cellulose. "Total cellulose" as used herein refers to the dry weight of the total cellulose either in the dispersion used for preparing the membrane, or in the final membrane or in the final layer.

The final membrane or layer comprising nanofibrillar cellulose, or the dispersion used for preparing the membrane, may contain additional ingredients, usually in minor amounts. In one example the membrane or the layer, or the dry matter of the dispersion, contains less than 1% (w/w) of additional ingredients, for example less than 0.5%, or less than 0.2%, or less than 0.1% of the total dry matter.

In one embodiment the membrane or the layer is a non-modified nanofibrillar cellulose membrane optionally comprising an amount of non-nanofibrillar chemical pulp in the range of 0.1-10% (w/w) of total cellulose, or in another range disclosed above.

Nanofibrillar Cellulose

The nanofibrillar cellulose is prepared normally from cellulose raw material of plant origin. The raw material may be based on any plant material that contains cellulose. The raw material may also be derived from certain bacterial fermentation processes. In one embodiment the plant material is wood. Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one embodiment the nanofibrillar cellulose is obtained from wood pulp. In one embodiment the nanofibrillar cellulose is obtained from hardwood pulp. In one example the hardwood is birch. In one embodiment the nanofibrillar cellulose is obtained from softwood pulp.

The nanofibrillar cellulose is preferably made of plant material. In one example the fibrils are obtained from non-parenchymal plant material. In such case the fibrils may be obtained from secondary cell walls. One abundant source of such cellulose fibrils is wood fibres. The nanofibrillated cellulose is manufactured by homogenizing wood-derived fibrous raw material, which may be chemical pulp. Cellulose fibers are disintegrated to produce fibrils which have the diameter of only some nanometers, which is 50 nm at the most and gives a dispersion of fibrils in water. The fibrils may be reduced to size where the diameter of most of the fibrils is in the range of only 2-20 nm. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging.

As used herein, the term "nanofibrillar cellulose" refers to cellulose fibrils or fibril bundles separated from cellulose-based fiber raw material. These fibrils are characterized by a high aspect ratio (length/diameter): their length may exceed 1 µm, whereas the diameter typically remains smaller than 200 nm. The smallest fibrils are in the scale of so-called elementary fibrils, the diameter being typically in the range of 2-12 nm. The dimensions and size distribution of the fibrils depend on the refining method and efficiency. Nanofibrillar cellulose may be characterized as a cellulose-based material, in which the median length of particles (fibrils or fibril bundles) is not greater than 50 µm, for example in the range of 1-50 µm, and the particle diameter is smaller than 1 µm, suitably in the range of 2-500 nm. In case of native nanofibrillar cellulose, in one embodiment the average diameter of a fibril is in the range of 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose may also contain small amounts of other wood components, such as hemicellulose or lignin. The amount is dependent on the plant source. Often used parallel names for nanofibrillar cellulose include nanofibrillated cellulose (NFC) and nanocellulose.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low, low viscosity vs. high viscosity etc. The fibrillation technique and the chemical pre-modification have an influence on the fibril size distribution. Typically, non-ionic grades have wider fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood (HW) vs. softwood (SW) pulp, different polysaccharide composition exists in the final nanofibrillar cellulose product. Commonly, the non-ionic grades are prepared from bleached birch pulp, which yields high xylene content (25% by weight). Modified grades are prepared either from HW or SW pulps. In those modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

In an aqueous environment, a dispersion of cellulose nanofibers forms a viscoelastic hydrogel network. The gel is formed at relatively low concentrations of, for example, 0.05-0.2% (w/w) by dispersed and hydrated entangled fibrils. The viscoelasticity of the NFC hydrogel may be characterized, for example, with dynamic oscillatory rheological measurements.

Regarding rheology, the nanofibrillar cellulose hydrogels are shear-thinning materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent on the raw material and the disintegration method. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives several successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one embodiment the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be, for example, Brookfield viscosity or zero shear viscosity.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used.

The nanofibrillar cellulose provided as a starting material in the method may be characterized by the viscosity it provides in a water solution. The viscosity describes, for example, the fibrillation degree of the nanofibrillar cellulose. In one embodiment the nanofibrillar cellulose when dispersed in water provides a Brookfield viscosity of at least 2000 mPa·s, such as at least 3000 mPa·s, measured at a consistency of 0.8% (w/w) and at 10 rpm. In one embodiment the nanofibrillar cellulose, when dispersed in water, provides a Brookfield viscosity of at least 10000 mPa·s measured at a consistency of 0.8% (w/w) and at 10 rpm. In one embodiment the nanofibrillar cellulose, when dispersed in water, provides a Brookfield viscosity of at least 15000 mPa·s measured at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at a consistency of 0.8% (w/w) and at 10 rpm.

In one embodiment the nanofibrillar cellulose comprises non-modified nanofibrillar cellulose. In one embodiment the nanofibrillar cellulose is non-modified nanofibrillar cellulose. It was found out that the drainage of non-modified nanofibrillar cellulose was significantly faster than with for example anionic grade. Non-modified nanofibrillar cellulose generally has a Brookfield viscosity in the range of 2000-10000 mPa·s, measured at a consistency of 0.8% (w/w) and at 10 rpm.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, that is, pulp.

The modification treatment to the fibers may be chemical or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface. The modification treatment may also be enzymatic.

The cellulose in the fibers may be especially ionically charged after the modification, because the ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. A cationic charge in turn may be created chemically by cationization by attaching a cationic group to the cellulose, such as quaternary ammonium group.

In one embodiment the nanofibrillar cellulose comprises chemically modified nanofibrillar cellulose, such as anionically modified nanofibrillar cellulose or cationically modified nanofibrillar cellulose. In one embodiment the nanofibrillar cellulose is anionically modified nanofibrillar cellulose. In one embodiment the nanofibrillar cellulose is cationically modified nanofibrillar cellulose. In one embodiment the anionically modified nanofibrillar cellulose is oxidized nanofibrillar cellulose. In one embodiment the anionically modified nanofibrillar cellulose is sulphonized nanofibrillar cellulose. In one embodiment the anionically modified nanofibrillar cellulose is carboxymethylated nanofibrillar cellulose.

The cellulose may be oxidized. In the oxidation of cellulose, the primary hydroxyl groups of cellulose may be oxidized catalytically by a heterocyclic nitroxyl compound, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

In one embodiment such chemically modified nanofibrillar cellulose, when dispersed in water, provides a Brookfield viscosity of at least 10000 mPa·s measured at a consistency of 0.8% (w/w) and at 10 rpm. In one embodiment such chemically modified nanofibrillar cellulose, when dispersed in water, provides a Brookfield viscosity of at least 15000 mPa·s measured at a consistency of 0.8% (w/w) and at 10 rpm. In one embodiment such chemically modified nanofibrillar cellulose, when dispersed in water, provides a Brookfield viscosity of at least 18000 mPa·s measured at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one embodiment the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at a consistency of 0.8% (w/w) and at 10 rpm.

In one embodiment the nanofibrillar cellulose comprises chemically unmodified nanofibrillar cellulose. In one embodiment such chemically unmodified nanofibrillar cellulose, when dispersed in water, provides a Brookfield viscosity of at least 2000 mPa·s, or at least 3000 mPa·s, measured at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one embodiment said nanofibrillar cellulose has a number average diameter of a fibril in the range of 1-100 nm. In one embodiment said nanofibrillar cellulose has a number average diameter of a fibril in the range of 1-50 nm. In one embodiment said nanofibrillar cellulose has a number average diameter of a fibril in the range of 2-15 nm, such as TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

In one example a rheometer viscosity of the nanofibrillar cellulose dispersion is measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s$^{-1}$ is exceeded. This method may be used for determining the zero-shear viscosity.

In one example the nanofibrillar cellulose, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, such as at least 10000 mPa·s, for example at least 15000 mPa·s measured at a consistency of 0.8% (w/w) and at 10 rpm.

The starting material for the membrane preparation process is usually nanofibrillar cellulose obtained directly from the disintegration of some of the above-mentioned fibrous raw material and existing at a relatively low concentration homogeneously distributed in water due to the disintegration conditions. The starting material may be an aqueous gel at a concentration of 0.3-5%, usually in the range of 0.3-0.5%. The gel of this type contains thus a great amount of water which may be removed so that a network of cellulose fibrils forming the body of a membrane and causing the structural integrity and strength properties of the membrane is left. This network may contain other solids as well that were originally dispersed in the aqueous gel, but the cellulose fibrils are the main constituent of the membrane.

Non-Nanofibrillar Pulp

A relative small amount of non-nanofibrillar cellulose in a dispersion comprising mainly nanofibrillar cellulose speeds up the draining time of the dispersion, for example in the manufacture of membranes. For example a share of one percent of non-nanofibrillar cellulose of the total cellulose could speed up the drainage even by about 50%, but at the minimum by about 15-20%. As the drying of a nanofibrillar cellulose is in general time-consuming and laborious, the drying process can be facilitated without substantially affecting to the properties of the membrane derived from the nanofibrillar cellulose.

This enables drying of nanofibrillar cellulose of relatively low consistency to a dry matter level where it can be used as a membrane. It is therefore possible to prepare nanofibrillar cellulose membranes in a time that is feasible in view of industrial production.

The non-nanofibrillar pulp refers to pulp which is not disintegrated into nanofibrillar form, or which contains mainly non-nanofibrillar cellulose. In general the non-nanofibrillar pulp is wood pulp.

In one embodiment the non-nanofibrillar pulp is unrefined or moderately refined pulp, which may be characterized for example by the pulp freeness, which measures the drainability of a pulp suspension. In general the freeness decreases with refining.

One example of defining the pulp properties comprises defining the drainability of a pulp suspension in water in terms of the Schopper-Riegler (SR) number (ISO 5267-1). The Schopper-Riegler test is designed to provide a measure of the rate at which a dilute suspension of pulp may be dewatered. It has been shown that the drainability is related to the surface conditions and swelling of the fibres, and constitutes a useful index of the amount of mechanical treatment to which the pulp has been subjected. The Schopper-Riegler number scale is a scale on which a discharge of 1 000 ml corresponds to a SR number of zero and zero discharge to a SR number of 100. In one embodiment the non-nanofibrillar pulp has a SR number in the range of 11-52.

Another method for the determination of drainability in terms of the Canadian Standard Freeness (CSF) number is specified in ISO 5267-2. CSF has been developed as a measure of groundwood quality. Generally, CSF decreases with refining, and it is sensitive to fines and water quality. Usually there is a correlation with the freeness and the length of the fibers: the lower the freeness, also the lower the fiber length. In one embodiment the non-nanofibrillar pulp has a CSF number in the range of 200-800 ml.

The non-nanofibrillar pulp may be mechanical or chemical pulp. In one embodiment the non-nanofibrillar pulp is chemical pulp. Even though mechanical pulp may be used, chemical pulp is more pure material and may be used in a wide variety of applications. Chemical pulp lack the pitch and resin acids present in mechanical pulp, and it is more sterile or easily sterilisable. Further, chemical pulp is more flexible and provides advantageous properties for example in medical patches or dressings and other materials applied on living tissue.

In one embodiment the non-nanofibrillar pulp is softwood pulp. Examples of softwood include spruce, pine or cedar. Softwood pulp contains longer fibers than hardwood pulp, such as over 2 mm long, which provide advantageous reinforcing properties in the membranes, such as enhanced tear strength.

In one embodiment the non-nanofibrillar pulp is chemical softwood pulp. In chemical softwood pulp the fiber length has been maintained thereby obtaining a mechanically durable but flexible material.

In one embodiment the membrane is a non-modified nanofibrillar cellulose membrane comprising non-nanofibrillar chemical pulp. In one embodiment the membrane is a non-modified nanofibrillar cellulose membrane comprising non-nanofibrillar chemical pulp in the range of 0.1-10% (w/w) of total cellulose.

In one embodiment the membrane comprises non-modified nanofibrillar cellulose and a portion of non-nanofibrillar chemical softwood pulp. In one embodiment the membrane comprises non-modified nanofibrillar cellulose obtained from hardwood and a portion of non-nanofibrillar chemical softwood pulp.

Preparation of the Layer Comprising Nanofibrillar Cellulose

The method for preparing the layer comprising nanofibrillar cellulose comprises first providing nanofibrillar cellulose and optionally any auxiliary agents, such as non-nanofibrillar pulp or other agents, and then forming a dispersion containing thereof in desired amounts. In one embodiment the dispersion is an aqueous dispersion. The dispersion is applied on the support to form a wet-laid web from the suspension onto the support. The dispersion is dried on the support to form the layer, which may also be called as membrane.

Said support may be a porous support, for example a filter, such as a filter fabric, which is impermeable to fibrils of the nanofibrillar cellulose but permeable to the liquid. There may also be a separate filter on a support. In one embodiment liquid from the dispersion is drained through the support. This may be carried out for example by applying reduced pressure though the support, such as by vacuum filtration. In one embodiment also heat is applied to the layer of dispersion or forming membrane, either completely or partly simultaneously with the reduced pressure, or as a subsequent step. Heat may be applied on the opposite side of the membrane sheet while continuing draining the liquid through the support by pressure difference over the support. In one example pressure is applied to the layer of dispersion or forming membrane by a heated surface. A membrane sheet will be formed during the drainage. In one example the dispersion is an aqueous dispersion. In one example the liquid comprises water.

Strong water retention is typical for nanofibrillar cellulose since water is bound to the fibrils through numerous hydrogen bonds. Consequently, reaching a desired dry matter content of a membrane may require a long drying time. Conventional methods such as vacuum filtration may involve several hours. Low consistency of the nanofibrillar cellulose dispersion favors the formation of thin membranes with small variations in grammage over the surface of the membrane. On the other hand this will increase the amount of water that has to be removed during drying.

The problem in mechanical water removal at slow rate is assumed to be the ability of nanofibrillar cellulose hydrogel to form a very dense and impermeable nanoscale membrane around itself, for example during filtration. The formed shell prevents diffusion of water from the gel structure, which leads to very slow concentration rates. The same applies to evaporation where the skin formation blocks the evaporation of water.

Due to the properties of the nanofibrillar cellulose hydrogels, either of native (chemically non-modified) or chemically modified cellulose, formation of membranes of uniform structure in short times that are suitable to industrial production is very challenging. In the present embodiments the water removal from a nanofibrillar cellulose hydrogel was improved.

The addition of a small amount of non-nanofibrillar pulp enhances the drainage of the liquid from the dispersion of nanofibrillar cellulose, which would otherwise be very challenging and time-consuming. However, to further enhance the drainage reduced pressure (vacuum) and heat may be used in combination. Further pressure may be used in combination with reduced pressure and/or heat.

One embodiment provides a method for preparing a membrane from nanofibrillar cellulose, comprising
  providing a dispersion of nanofibrillar cellulose, optionally comprising an amount of non-nanofibrillar pulp in the range of 0.1-60% (w/w) of total cellulose,
  supplying said dispersion on a filter fabric support that is impermeable to fibrils of the nanofibrillar cellulose but permeable to the liquid,
  draining liquid from a nanofibrillar cellulose dispersion by effect of reduced pressure through the filter fabric to form a membrane sheet on the filter fabric,
  applying heat on the opposite side of the membrane sheet to the membrane sheet while continuing draining of the liquid through the filter fabric by pressure difference over the filter fabric, such as by the effect of reduced pressure through the filter fabric. This method may be used for preparing the first layer comprising nanofibrillar cellulose and/or the second layer comprising nanofibrillar cellulose.

It was noticed that even 1% of non-nanofibrillar pulp was enough to speed up the drainage by even 50%, in general in the range of 10-50%, and no substantial further effect was noticed with higher pulp additions. Therefore it is possible to keep the amount of the non-nanofibrillar pulp low, for example in the range of 0.1-3%, or 0.5-3%, or 1-3%, or 0.5-2% or 0.2-1.5%. However, to obtain desired properties of the final product, such as the high tear strength of the membrane, also higher portions of non-nanofibrillar cellulose may be used. The amount of the non-nanofibrillar pulp refers to a percentage calculated from the weight of total cellulose or fiber material content in the dispersion or in the membrane.

In one embodiment a membrane is prepared starting from a nanofibrillar cellulose dispersion in liquid medium comprising a portion of non-nanofibrillar pulp by first draining the liquid by effect of reduced pressure through a filter fabric impermeable to fibrils of the nanofibrillar cellulose but permeable to the liquid to form a membrane sheet on the filter fabric, whereafter heat is applied on the opposite side of the membrane sheet while continuing draining of the liquid through the filter fabric by pressure difference over the filter fabric. When the membrane sheet has attained a desired dry matter content may be removed from the filter fabric as a freestanding membrane which may be treated further or stored. A "nanofibrillar cellulose dispersion" as used herein in the context of the preparation method of a membrane refers to a nanofibrillar cellulose dispersion optionally containing a portion of the non-nanofibrillar pulp, as described herein, and other possible ingredients.

In one embodiment the method comprises removing the membrane sheet from the support, such as a filter fabric, as a freestanding membrane comprising nanofibrillar cellulose.

The heat applied on the opposite side of the membrane sheet being formed through draining may be accomplished by contact (conduction) with a heated surface, i.e. by conduction of heat from a heated surface, or by irradiation of the surface of the membrane sheet i.e. with radiation heat. At the same time, the liquid is drained through pressure difference that exists on the opposite sides of the filter fabric. This may be accomplished by reduced pressure or pressing mechanically the membrane sheet with the heated surface.

In one embodiment the heat applied on the opposite side of the membrane sheet to the membrane sheet is accomplished by contact of the surface of the membrane sheet with a heated surface.

In one embodiment the heat applied on the opposite side of the membrane sheet to the membrane sheet is accomplished by contact of a heated surface with a layer interposed between the heated surface and the membrane sheet, such as a gauze, a filter fabric or a structural layer to which the membrane is to be laminated.

In one embodiment pressure is also applied by the heated surface to the membrane sheet, said pressure causing at least partly the pressure difference over the filter fabric.

In one embodiment liquid is drained from the membrane sheet through the filter fabric by the effect of reduced pressure while pressure is being applied by the heated surface to the membrane sheet, said reduced pressure and the pressure applied by the heated surface causing together the pressure difference over the filter fabric.

In one embodiment liquid is drained from the membrane sheet through the filter fabric to at least one adsorbent sheet while pressure is being applied by the heated surface to the membrane sheet, said pressure applied by the heated surface causing the pressure difference over the filter fabric.

In one embodiment the liquid is drained from the membrane sheet by the effect of reduced pressure to opposite directions through both surfaces of the membrane sheet.

The heat is applied to the membrane sheet being formed to raise its temperature to the range which is below the boiling point of the liquid to promote the removal of the liquid in liquid state. In one embodiment the temperature of the membrane sheet is kept under 100° C. by the heat applied to the membrane sheet.

If the pressure difference is achieved by pressing the membrane sheet with the heated surface against the filter fabric, and the final draining of the liquid out of the membrane sheet may be enhanced by placing an absorbent sheet against the free side of the filter fabric where it may receive the liquid issuing through the fabric. Absorbent pulp sheets, blotting papers or drying felts that can receive water can be used. Such sheets may be placed in layers against the free side of the filter fabric. Such an absorbent sheet or plurality of sheets remove liquid by absorption from the membrane sheet being formed.

In one embodiment the heat and pressure are applied to opposite sides of the membrane sheet.

Some grades of the nanofibrillar cellulose are especially hard to dry because of their water retention capacity and the drying may take considerably longer than with normal "native" grades. Nanofibrillar cellulose containing anionically charged groups are one example of nanofibrillar cellulose dispersions that are particularly difficult to dry. Cellulose obtained through N-oxyl mediated catalytic oxidation (e.g. through 2,2,6,6-tetramethyl-1-piperidine N-oxide) or carboxymethylated cellulose are specific examples of anionically charged nanofibrillar cellulose where the anionic charge is due to a dissociated carboxylic acid moiety. These anionically charged nanofibrillar cellulose grades are potential starting materials for the preparation of membranes, because high quality nanofibrillar cellulose dispersions are easy to manufacture from the chemically modified pulp. The anionically charged nanofibrillar cellulose grades may be pretreated by lowering the pH of the dispersion by adding acid. This pretreatment reduces the water retention capacity. For example by lowering the pH of the nanofibrillar cellulose dispersion to below 3 the drying time using the above-described methods can be reduced. In one embodiment the nanofibrillar cellulose dispersion where the cellulose contains anionically charged groups is pretreated by lowering its pH, whereafter the pretreated nanofibrillar cellulose dispersion is supplied at the lowered pH on the filter fabric.

If the size of the cellulose fibrils is small, they may flow through the filter fabric together with the liquid to be removed even at the smallest possible hole size of the filter fabric. According to one embodiment of the method, the cellulose fibrils are kept separated from the filtrate liquid by applying a first nanofibrillar cellulose dispersion on the filter fabric and forming a fibril network through draining of the liquid through the filter fabric that is impermeable to the fibrils of the first nanofibrillar cellulose dispersion. This fibril network acts as a kind of auxiliary filter for the second nanofibrillar cellulose dispersion applied subsequently where the size of the fibrils is smaller than in the first nanofibrillar cellulose dispersion. After the application of the second nanofibrillar cellulose dispersion the draining proceeds as with a nanofibrillar cellulose dispersion applied in one step.

In one embodiment the first nanofibrillar cellulose dispersion is first supplied on the filter fabric and liquid is drained from it to form a fibril network, whereafter a second nanofibrillar cellulose dispersion where the size of the fibrils is smaller than the size of the fibrils of the first nanofibrillar cellulose dispersion is supplied on said fibril network and liquid is drained through said fibril network and the filter fabric from the second nanofibrillar cellulose dispersion.

The size of the fibrils of the second nanofibrillar cellulose dispersion is such that compared with the mesh size or aperture size of the filter fabric they would penetrate through the fabric together with the liquid (filtrate) drained from the dispersion. The proportion of the second nanofibrillar cellulose dispersion is greater than the proportion of the first nanofibrillar cellulose dispersion and it constitutes the largest part of the weight of the dried membrane. The size of the fibrils may refer to the diameter of the fibrils or the length of the fibrils, or to both the diameter and the length of the fibrils.

In one embodiment the fibrils of the second fibril dispersion are of such size that they are capable of penetrating through the filter fabric if the second fibril dispersion would be supplied directly to the filter fabric.

A filter fabric that has hole or aperture size sufficiently small in relation to the particle size (size of the fibrils) can be used so that the fabric divides by its permeability characteristics (cut-off value) the nanofibrillar cellulose dispersion in filtrate substantially devoid of fibrils and filtered membrane sheet consisting of cellulose fibrils and possible other solid matter contained in the nanofibrillar cellulose dispersion. The hole or aperture size of such filter fabrics are in the micrometer range. The filter fabric is made of a material that is non-adherent to the filtered nanofibrillar cellulose membrane sheet. Plastics may be used as the material of the filter fabric. Tightly woven polyamide-6,6 fabrics are one example of filter fabrics that can be used. Such polyamide fabrics are available in various hole sizes, which may be selected according to the particle size of the nanofibrillar cellulose. The filter fabric may also be called as filter layer or filter fabric layer.

The heated surface for bringing heat into the nanofibrillar cellulose is also non-adherent to the filtered nanofibrillar cellulose membrane sheet. A metal plate coated with a repellent and heat-resistant coating, for example PTFE, may be used, or even a sheet of PTFE alone, for example having a thickness of about 1 mm.

In one embodiment the liquid is drained from the membrane sheet through the filter fabric by the effect of reduced pressure, while heat applied on the opposite side of the membrane sheet to the membrane sheet is accomplished by radiation heat to the membrane sheet, said reduced pressure causing the pressure difference over the filter fabric.

The method may be used for manufacturing separate individual membranes successively one by one in a sheet mold by applying the nanofibrillar cellulose dispersion on a filter fabric and performing successive work stages according to a predetermined sequence, or for manufacturing continuous membrane in a continuous process by applying the nanofibrillar cellulose dispersion on a moving filter fabric which carries the membrane sheet being formed through successive work stages.

In one embodiment the nanofibrillar cellulose suspension is supplied to a moving filter fabric as a continuous layer and continuous membrane is produced by carrying the continuous layer by the moving filter fabric through different processing steps, whereafter the membrane is separated from the filter fabric.

In one embodiment the membrane sheet is removed together with the filter fabric from a sheet mold where the nanofibrillar cellulose dispersion was supplied and placed in a press where the membrane sheet is dried to a freestanding membrane.

In one embodiment the membrane sheet is removed from any filter layer through which the liquid has been removed from the nanofibrillar cellulose dispersion or from the membrane sheet, to form a freestanding nanofibrillar cellulose membrane In one embodiment the membrane sheet is dried to a freestanding membrane in a sheet mold where the nanofibrillar cellulose dispersion was supplied.

The starting concentration of the nanofibrillar cellulose dispersion, usually aqueous dispersion, that is applied on the filter fabric may be in the range of 0.1-10%. However, it is usually not higher than 5%, for example in the range of 0.3-5.0%, for example about 0.4%. This is usually the initial concentration of the nanofibrillar cellulose at the exit of the manufacturing process where it is manufactured by disintegrating fibrous raw material. However, it is possible that the nanofibrillar cellulose dispersion is diluted with a liquid from the initial concentration (concentration of the product from the manufacturing process) to a suitable starting concentration to ensure that it is distributed evenly on the filter fabric to avoid variations in the membrane structure. Depending on the characteristic viscosity of the nanofibrillar cellulose grade, the starting concentration may be lower or higher, and it may be in the range of 0.1-10%. Higher concentrations may be used for low-viscosity grades, which may be spread uniformly on the filter fabric despite the high concentration. The nanofibrillar cellulose issues as aqueous nanofibrillar cellulose from a manufacturing process where the fibrous starting material suspended in water is disintegrated. Draining of the liquid out of the nanofibrillar cellulose dispersion may be called "dewatering" in the case of water or aqueous solution.

When water is the liquid to be drained, the heat is applied to the nanofibrillar cellulose on the filter fabric preferably at the intensity that raises the temperature of the nanofibrillar cellulose at least to 70° C. but below 100° C., for example in the range of 70-95° C. Contrary to what might be expected, raising the temperature above 100° C. does not improve the drying result, because as long as the membrane sheet contains large amounts and water and the water is removed through pressure difference in the initial stages of drying, water must not be allowed to boil, because this will have a detrimental effect on the membrane. When the membrane sheet is dry enough and no further water is extractable from the sheet by pressure difference, the residual water still bound to the finally formed fibril network of the sheet can be removed by evaporation. In this case temperature higher than 100° C. can also be used.

The filter fabric is of the type that does not adhere to the membrane sheet of nanofibrillar cellulose. Synthetic polymer materials such as PET, polyamide and fluoropolymers are suitable materials.

Auxiliary agents for enhancing the manufacturing process or improving or adjusting the properties of the membrane may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or added to a nanofibrillar cellulose dispersion before applying it on the filter fabric. The auxiliary agents may be also added to the final membrane product, for example by impregnating. Examples of auxiliary agents include therapeutic and cosmetic agents and other agents affecting to the properties of the nanofibrillar cellulose layer or membrane or to the properties of the active agents, such as surfactants, plasticizers, emulsifiers or the like.

To form a solid free-standing membrane where cellulose fibrils are arranged in a network, liquid must be removed. In one embodiment the liquid is removed from nanofibrillar cellulose comprising a portion of non-nanofibrillar pulp by a method comprising two steps. In the first step liquid is drained by reduced pressure from a nanofibrillar cellulose dispersion comprising a portion of non-nanofibrillar pulp through a filter fabric impermeable to the fibrils which causes the formation of a wet membrane sheet still containing large amounts of liquid. In the second step heat is applied on the opposite side of the membrane sheet while a pressure difference is maintained over the filter fabric, causing the drainage from the membrane sheet to continue.

Compared with dewatering of nanofibrillar cellulose dispersions where the cellulose is native cellulose, dewatering of nanofibrillar cellulose dispersions where the cellulose is anionically charged cellulose is even more time-consuming because water is bound very strongly to the cellulose. Nanofibrillar cellulose containing anionically charged groups can be for example chemically modified cellulose that contains carboxyl groups as a result of the modification. Cellulose obtained through N-oxyl mediated catalytic oxidation (e.g. through 2,2,6,6-tetramethyl-1-piperidine N-oxide, known by abbreviation "TEMPO") or carboxymethylated cellulose are examples of anionically charged nanofibrillar cellulose where the anionic charge is due to a dissociated carboxylic acid moiety. If embodiments of When making membranes from nanofibrillar cellulose containing anionic groups, the total drying time is expected be many times the total drying time with nanofibrillar cellulose where the cellulose is unmodified, mainly due to the higher water retention capacity and higher viscosity of the anionically charged nanofibrillar cellulose. For example dewatering unmodified nanofibrillar cellulose in the first step when the target is a 20 gram per square meter membrane takes less than 60 seconds (time from starting the vacuum until no visible water is seen on the membrane sheet), whereas dewatering of a anionically charged nanofibrillar cellulose for a membrane with the same target grammage in similar conditions may take even 60 to 120 minutes.

The dewatering properties of these anionically charged nanofibrillar cellulose grades may be considerably improved by pretreating the nanofibrillar cellulose dispersion by an acid. When the nanofibrillar cellulose contains anionically charged groups that act as bases (acid moieties in dissociated from), as is the case with oxidized cellulose and carboxymethylated cellulose, lowering the pH with acid will convert these groups to undissociated form, the electrostatic repulsion between the fibrils is no more effective, and the water-fibril-interaction is changed in a way that favors the dewatering of the dispersion (water retention capacity of the dispersion is reduced). The pH of the anionically charged nanofibrillar cellulose dispersion is lowered below 4, preferably below 3, to improve the dewatering properties.

Anionically charged nanofibrillar cellulose dispersion which was obtained from "TEMPO" oxidized pulp needed a dewatering time under vacuum of roughly 100 minutes at original (unadjusted) pH, when the target grammage of the membrane was 20 grams per square meter. When the pH of the dispersion was lowered to 2 with HCl before the dewatering, the dewatering time in the same conditions was about 30 seconds, that is, the time was reduced to 0.5% of the original. The dispersion becomes visibly aggregated (fibril flocks are formed) when the pH is lowered, which is believed to be one reason for faster dewatering because water flows more easily between the aggregates.

The membrane sheets formed in the first step by dewatering the dispersion where the pH is lowered can be dried to final dryness in the second step. The tendency of the membranes to tear during the final stages of the drying, which is probably due to the initially aggregated structure of the dispersion at low pH, may be eliminated by interrupting the drying. The membrane sheet is then allowed to lie free and detached from any supporting structure (such as filter fabric) to relieve the stresses. Thereafter the drying may be continued. The final stages of the drying may be performed between two absorbent sheets (for example blotting papers) at a temperature above 100° C., for example at 105° C., to remove the remaining moisture.

If the fibril size of the anionically charged nanofibrillar cellulose is too small with regard to the filtration capacity of the filter fabric (cutoff size), which often is the case with nanofibrillar cellulose made from oxidized pulp, an auxiliary filter layer can first be formed of nanofibrillar cellulose dispersion with larger fibril size on the same principle as explained above, before the pretreated nanofibrillar cellulose dispersion is added. The auxiliary filter layer may be made for example of chemically unmodified (native) nanofibrillar cellulose dispersion where the fibril size is larger.

When the nanofibrillar cellulose dispersions are applied to the filter fabric, they may be applied by pouring, or some other application methods for making initially a uniform layer of the dispersion with minimal thickness variations may be used. The dispersions may for example be sprayed on the filter fabric. If necessary, the dispersion may be diluted with water to decrease the viscosity and improve the uniform spreading of the dispersion.

When the membrane is separated from the filter fabric through which the water has been filtered under its formation, a freestanding membrane comprising nanofibrillar cellulose is formed. However, it is also possible that the filtration takes place through a gauze that will remain as a structural part of the membrane product. In this case the adhesion between the gauze and the membrane sheet during its dewatering is desirable. The gauze may also be on top of the formed membrane sheet.

The membrane that has been formed to a freestanding membrane may be in a later phase laminated to a sheet of another material. These nanofibrillar cellulose membranes may also be laminated together to form a thicker nanofibrillar cellulose membrane.

In one embodiment the membrane has a density in the range of 600-1050 kg/m$^3$. In one embodiment the membrane has a density in the range of 900-1050 kg/m$^3$. In one embodiment the membrane has a density in the range of 990-1050 kg/m$^3$. The addition of pulp fibers lower the density.

Thin membranes with uniform grammage distribution (small grammage variation over the area of the membrane) may be prepared by the method. The thickness of the membranes is usually no higher than 100 μm, for example no higher than 70 μm, for example in the range of 5 to 100 μm. If a freestanding membrane is prepared, the thickness may be in the range of 10 to 50 μm and still more preferably 20 to 50 μm to confer it sufficient strength, whereas when forming a membrane layer in a membrane product its thickness can be lower, in the range of 5 to 40 μm.

In one embodiment the grammage of the membrane is in the range of 40-80 g/m$^2$. In one embodiment the grammage of the membrane is in the range of 50-60 g/m$^2$.

In general the tear index of the membrane is in the range of 0.5-4.0 mNm$^2$/g. The value of about 0.5 mNm$^2$/g is achieved when the membrane has very little or no pulp fibers. With about 10% of pulp fibers the tear index in usually in the range of about 3-4 mNm$^2$/g. In one embodiment the tear index of the membrane is in the range of 1.0-4.0 mNm$^2$/g. In one embodiment the tear index of the membrane is in the range of 1.0-3.0 mNm$^2$/g. However, such a tear index is too low to enable the use of such a membrane alone in medical purposes. For example the membrane may be torn during the application onto the skin, and at least when it is removed from the skin.

The nanofibrillar cellulose of the membrane may be crosslinked. The tensile strength index of the membrane is higher than 35 Nm/g at 85% relative humidity, such as higher than 50 Nm/g at 85% relative humidity.

The membrane comprising nanofibrillar cellulose may constitute exclusively or substantially of cellulosic material. It is possible that some auxiliary agents originally present in the dispersion either in dissolved or solid form will be included in the membrane, provided that they do not interfere with the strength properties of the membrane. In case of other solid agents, they are preferably other substances than cellulose or their derivatives, the nanofibrillar cellulose being the main cellulose-based solid substance in the membrane. Soluble substances that may be used include water-soluble polymers. Polymers in latex form may also be used as one structural constituent.

Preparation of the Medical Multi-Layer Product

The membranes prepared as explained above may be used as membranes or layers comprising nanofibrillar cellulose when preparing the medical multi-layered structures. In one example existing layers, such as moisture-containing or dry or dried layers, are laminated together. In one example overlaying layers are formed in a dewatering process.

In general the medical multi-layer product comprises at least two layers. One embodiment provides a medical multi-layer product comprising a (first) layer comprising nanofibrillar cellulose, and
a layer of gauze.

The medical multi-layer product may also comprise three layers. One embodiment provides such a medical multi-layer product further comprising a second layer comprising nanofibrillar cellulose. In one embodiment the layer of gauze is between the first layer comprising nanofibrillar cellulose and the second layer comprising nanofibrillar cellulose. The layers may also have any other order, such as a layer of gauze and two layers comprising nanofibrillar cellulose, or a first layer comprising nanofibrillar cellulose, a layer of gauze, a second layer comprising nanofibrillar cellulose and a third layer comprising nanofibrillar cellulose, or a first layer comprising nanofibrillar cellulose, a second layer comprising nanofibrillar cellulose, a layer of gauze, and a third layer comprising nanofibrillar cellulose. Two adjacent layers comprising nanofibrillar cellulose may be similar or different, for example they may have different thicknesses, concentrations, compositions, moisture contents or other properties, or they may contain different agent(s) or one layer may not contain an agent while the other one does, or a combination of these features. In one example one layer comprises non-modified nanofibrillar cellulose and other layer comprises modified nanofibrillar cellulose, such as anionically modified nanofibrillar cellulose. The medical multi-layer product is in general provided as sheets, which are or may be cut into desired sizes and/or shapes. The final product is provided as a dried product, which usually have a desired moisture content, and the product may be moisturized prior to use. In one embodiment the multi-layer products described herein do not contain any other layers, adhesives or the like between the mentioned layers, so the mentioned layers are next to each other, or in direct contact with each other, i.e. the multi-layer product consists of the mentioned layers.

One embodiment provides a method for preparing a medical multi-layer product, said method comprising providing a layer comprising nanofibrillar cellulose,
providing a layer of gauze, and
laminating the layer comprising nanofibrillar cellulose and the layer of gauze to obtain the medical multi-layer product. The layer comprising nanofibrillar cellulose may also be called for example as a membrane layer comprising nanofibrillar cellulose or as a membrane comprising nanofibrillar cellulose. This layer may be called as a first layer comprising nanofibrillar cellulose if another further layer(s) comprising nanofibrillar cellulose is/are to be added to the product.

The method may also include the preparation of the membrane comprising nanofibrillar cellulose. One embodiment provides a method for preparing a medical multi-layer product, said method comprising providing nanofibrillar cellulose,
optionally providing non-nanofibrillar pulp,
forming a dispersion of nanofibrillar cellulose optionally comprising an amount of non-nanofibrillar pulp, for example in the range of 0.1-60% (w/w) of total cellulose, and
drying the dispersion on a support to form a layer comprising nanofibrillar cellulose,
providing a layer of gauze, and
laminating the layer comprising nanofibrillar cellulose and the layer of gauze to obtain the medical multi-layer product. The layer of gauze may be provided before drying the dispersion or it may be applied after the drying.

In one embodiment the method further comprises providing a second layer comprising nanofibrillar cellulose, and laminating the first layer comprising nanofibrillar cellulose, the layer of gauze and the second layer comprising nanofibrillar cellulose to obtain a medical multi-layer product. In one embodiment the layer of gauze is between the first layer comprising nanofibrillar cellulose and the second layer comprising nanofibrillar cellulose. In one embodiment the first and the second layers comprising nanofibrillar cellulose are next to each other. The method may also comprise forming or adding the second layer comprising nanofibrillar cellulose in a similar way as the first layer is formed. The first and the second layer may be identical or they may be different.

Lamination refers to manufacturing of material in multiple layers. A laminate is a permanently assembled object by heat, pressure, welding, adhesives, or by physico-chemical adhesion e.g. hydrogen bonding. The layer comprising nanofibrillar cellulose and the layer of gauze may be attached to each other by hydrogen bonds, especially when a gauze containing natural fibers is used. A composite product is obtained. In one embodiment the laminate contains no adhesive or adhesive has not been used in the lamination.

In one embodiment the laminating comprises stratifying or layering. A layer comprising nanofibrillar cellulose may be prepared by providing a dispersion comprising the nanofibrillar cellulose and any further ingredients, such as non-nanofibrillar pulp, one or more therapeutic or cosmetic agent(s), fillers, colorants, or other ingredients, and dewatering the dispersion to a desired moisture or dry content with a suitable dewatering method. The dewatering may be carried out through a gauze to attach the layer comprising nanofibrillar cellulose to the gauze. Any of the dewatering methods described herein may be used. The dispersion may be provided as a gel, such as a hydrogel.

A layer comprising nanofibrillar cellulose, or also the medical multi-layer product, may have a moisture content in the range of 0-20% (w/w), such as 1-20% (w/w), 5-20% (w/w), 0-15% (w/w), such as 1-15% (w/w), 5-15% (w/w), or 0-10% (w/w), such as 1-10% (w/w), or 5-7% (w/w). Higher moisture content would make the layer comprising nanofibrillar cellulose prone to crack. Such moisture content may be obtained by any suitable dewatering method and a layer having such moisture content may be prepared by any suitable method or device, for example by the ones described herein. In one example the layer comprising nanofibrillar cellulose is provided, such as prepared and/or applied, by extrusion, such as by using an extruder. The layer may be extruded onto a layer of gauze or onto an existing layer of nanofibrillar cellulose, and laminated, i.e. attached, onto said layer. The extruder may be a film extruder or a sheet extruder. A suitable die is used, for example a T-shaped die or a coat hanger die. Co-extrusion may be used to apply one or more layers comprising nanofibrillar cellulose, for example two or three layers, on top of a gauze or on top of a layer comprising nanofibrillar cellulose.

One embodiment provides a method for preparing a medical multi-layer product, the method comprising
- providing a filter, such as a filter fabric,
- providing a dispersion comprising nanofibrillar cellulose, such as a gel,
- providing a gauze,
- applying the dispersion onto the filter,
- applying the gauze onto the dispersion, and
- dewatering the structure through the filter to obtain the medical multi-layer product.

One embodiment provides a method for preparing a medical multi-layer product, the method comprising
- providing a filter, such as a filter fabric,
- providing a gauze,
- providing a dispersion comprising nanofibrillar cellulose, such as a gel,
- applying the gauze onto the filter,
- applying the dispersion onto the gauze, and
- dewatering the structure through the filter to obtain the medical multi-layer product.

Further layers of dispersions comprising nanofibrillar cellulose may be formed. The further layers may have the same composition as the first layer, or they may be different. For example one layer may contain therapeutic or cosmetic agent and another layer does not, or it may contain a different therapeutic or cosmetic agent.

One embodiment provides a method for preparing a medical multi-layer product, the method comprising
- providing a filter, such as a filter fabric,
- providing a gauze,
- providing a first dispersion comprising nanofibrillar cellulose, such as a gel,
- providing a second dispersion comprising nanofibrillar cellulose, such as a gel, which may be same or different than the first dispersion comprising nanofibrillar cellulose,
- applying the first dispersion onto the filter,
- applying the gauze onto the first dispersion,
- applying the second dispersion onto the gauze, and
- dewatering the structure through the filter to obtain the medical multi-layer product. An obtained intermediate product is shown in FIG. 1, wherein it can be seen how the first and the second layers of nanofibrillar cellulose overlap on one side of the product outside the gauze area. The overlaps may be further cut to obtain the final product. The gauze was a perforated non-woven viscose-polyester gauze.

When a gauze is between two layers both comprising nanofibrillar cellulose, the nanofibrillar celluloses in the two layers may contact each other through the gauze thereby adhering strongly together. The gauze is completely covered with the layers comprising nanofibrillar cellulose so the gauze will not be adhered to a skin or to a wound in the skin during the use. Also the product may be applied onto the skin with either side towards the skin. However, one side of the product may contain a thicker layer of nanofibrillar cellulose which is meant to be applied against the skin. This side may be indicated in the product, for example by marking the side or the other side with text, figures, colours or the like.

The dewatering may be carried out by applying vacuum through the filter, or by applying pressure to the layers, either from one or from two (opposite) sides, or by applying heat, or by a combination thereof. The dewatering methods of a membrane comprising nanofibrillar cellulose described herein may be applied to the layering process. The filter fabric may be as described herein.

The gauze as used herein refers to any suitable gauze, such as a fabric, a cloth or the like material comprising fibers. The gauze may be woven or nonwoven, sterile or nonsterile, plain or impregnated, or fenestrated (perforated or with slits), or a combination thereof.

In one embodiment the gauze is woven. By one definition a woven gauze is a thin, translucent fabric with a loose open weave. In technical terms a woven gauze is a weave structure in which the weft yarns are arranged in pairs and are crossed before and after each warp yarn keeping the weft firmly in place. The gauze may comprise natural fibers, semi-synthetic fibers or synthetic fibers, such as viscose, rayon, polyester and the like, or combinations thereof, for example a viscose-polyester mixture. When used as a medical dressing, gauze may be made of cotton. The gauze may also act as a pad of a patch. In one embodiment the gauze is viscose-polyester gauze, for example non-woven. Such a non-woven gauze is very porous and permeable and it is moderately elastic providing irreversible elongation in one direction. In one embodiment the gauze is nonwoven. Non-woven gauze comprises fibers pressed together to resemble a weave, which provides improved wicking and greater absorbent capacity. Compared to woven gauze, this type of gauze produces less lint and has the benefit of leaving fewer fibers behind in a wound when removed. Examples of nonwoven gauze dressings include gauzes made of polyester, viscose, or blends of these fibers which are stronger, bulkier, and softer than woven pads.

The gauze used in the embodiments may comprise absorbing material, for example to enable the medical product to absorb exudate, to soak up blood, plasma, and other fluids exuded from the wound and containing them in one place. The gauze may also stem bleeding and to help sealing a wound. The gauze may also absorb a therapeutic agent or other agent.

In one embodiment the gauze comprises natural fibers or natural-fiber-based material, such as cotton, cellulose, linen, silk or the like. Natural fibers provide free hydroxyl groups which helps attaching the gauze to the layer(s) comprising nanofibrillar cellulose via hydrogen bonds. Also semi-synthetic fibers may provide free hydroxyl groups, such as viscose.

The gauze should be highly permeable allowing fluids to pass through. The gauze is not a filter and it does not limit the flow through of most macromolecules. The gauze may not be used as a filter for dewatering a dispersion comprising nanofibrillar cellulose. The gauze may be porous and/or it may be fenestrated having perforations or slits or the like. A paper or cardboard is not a gauze. More particularly paper is not suitable as paper does not provide high enough tear strength in such grammages or thicknesses which would be suitable for the multi-layer products. The same applies to cardboard or other similar cellulosic products. In one embodiment the gauze is non-cellulosic.

In one example the gauze is resilient. Many natural, semi-synthetic or synthetic fibers are resilient. However, in one example the gauze is rigid providing non-resilient properties, for example when it comprises cotton. The gauze may provide reinforcing properties, for example to enhance the tear strength of the multi-layer product.

Tear strength (tear resistance) is a measure of how well a material can withstand the effects of tearing. More specifically it measures how well a material resists the growth of any cuts when under tension. Tear resistance may be measured by the ASTM D 412 method (the same may be used to measure tensile strength, modulus and elongation). Also a tear index may be presented, wherein tear index=tear strength/grammage, and it is usually measured in $mNm^2/g$.

The gauze may have a tear strength in the range of 1500-2000 mN, such as 1700-1900 mN. The gauze may have a tear index in the range of 50-60 $mNm^2/g$. Tear index may be measured with ISO 1974. The tensile strength of a gauze may be for example in the range of 0.8-1.5 kN/m, such as 1-1.2 kN/m. Tensile strength may be measured by ISO 1924-3. The gauze may have a grammage in the range of 20-50 $g/m^2$, for example in the range of 20-40 $g/m^2$ or 20-30 $g/m^2$. Grammage may be measured by ISO 536. The gauze may have a density for example in the range of 270-350 $g/cm^3$, such as in the range of 290-330 $g/cm^3$. Also a bulk may be presented as $cm^3/g$, measured by ISO 534.

A layer of gauze, such as a dry gauze, may have a thickness in the range of 100-1000 µm, such as 100-200 µm, 150-200 µm, 200-300 µm, 300-400 µm, 400-500 µm, 500-600 µm, 600-700 µm, 700-800 µm, 800-900 µm or 900-1000 µm. However, thicker gauzes may also be used, for example up to 2000 or 3000 µm. In one embodiment the thickness of the gauze is in the range of 100-200 µm, such as 100-120 µm, 120-140 µm, or 140-160 µm or 160-190 µm. However, when the gauze was combined with the layer(s) comprising nanofibrillar cellulose, the total thickness of the final dry multi-layer product could be lower than the thickness of the dry gauze alone.

The medical multi-layer product may have a thickness in the range of 100-1000 µm. Even thicker products may be prepared, for example having a thickness of about 1500 µm, 2000 µm, 2500 µm or 3000 µm. In one embodiment the medical multi-layer product has a thickness in the range of 100-500 µm, such as 100-400 µm, 100-300 µm, 100-200 µm, or 120-180 µm, for example 120-150 µm, 120-140 µm or 130-140 µm. In general the thickness of the gauze layer in the final product may be in the range of 100-1000 µm, such as 100-200 µm, 150-200 µm, 200-300 µm, 300-400 µm, 400-500 µm, 500-600 µm, 600-700 µm, 700-800 µm, 800-900 µm or 900-1000 µm. In one example the thickness of the gauze layer in the product is in the range of 100-160 µm, such as 140-160 µm, for example about 150 µm. In one example the thickness of the gauze layer in the product is in the range of 100-120 µm, for example about 105 µm. Thickness may be measured as bulking thickness by ISO 534.

In the multi-layer products the membranes comprising nanofibrillar cellulose may have a variety of thicknesses depending on desired properties of the product, such as absorption capacity, stiffness, etc. If there are more than one such membranes the membranes may have different thicknesses. For example the membrane which is in contact with the skin during the use may have higher thickness than the membrane which is at the other side of the gauze. In one embodiment the membrane has a thickness in the range of 5-60 µm. The thickness of a membrane which is in contact with the skin may be in the range of 20-60 µm or 20-50 µm, for example 30-40 µm. Usually if a membrane has a thickness over 60 µm the stiffness increases and the membrane may not be suitable for all the uses described herein. However, in some cases it may be possible to use thicker membranes, such as up to 100 µm, or even up to 150 or 200 µm, for example in the range of 40-80 µm, 50-100 µm, 20-200 µm, 50-150 µm, 50-200 µm or 100-200 µm. The thickness of a membrane which is at the other side of the product may be in the range of 5-10 µm. This membrane may be thinner because one of its main functions is to seal the product in such way that the gauze is not exposed. A thin membrane however does not have a remarkable effect to the elasticity of the product. The thicker membrane which is against the skin has more functional properties, such as absorption capacity, permeability and interaction with the skin. The thickness of a layer, for example a nanofibrillar layer, may be determined from a final product for example by dying and/or microscopically.

In one embodiment the multi-layer product comprises a first layer comprising nanofibrillar cellulose having a thickness in the range of 20-60 µm, a layer of gauze having a thickness in the range of 140-160 µm, and a second layer comprising nanofibrillar cellulose having a thickness in the range of 5-10 µm.

In one embodiment the multi-layer product comprises a first layer comprising nanofibrillar cellulose having a thickness in the range of 20-60 µm, a layer of gauze having a thickness in the range of 100-120 µm, and a second layer comprising nanofibrillar cellulose having a thickness in the range of 5-10 µm.

With a reinforcing gauze the tear index of the medical structure is remarkably higher. In one embodiment the medical multi-layer product has a tear index in the range of 18-100 $mNm^2/g$. In one embodiment the medical multi-layer product has a tear index in the range of 20-70 $mNm^2/g$. The tear index may be different in one direction and in a perpendicular direction, which may be affected by the properties of the gauze. For example a gauze may have different properties to the perpendicular directions, which may be called as machine direction and cross direction.

In one embodiment the medical multi-layer product has a grammage in the range of 50-100 $g/m^2$. In one embodiment the medical multi-layer product has a grammage in the range of 60-80 $g/m^2$, for example in the range of 64-75 $g/m^2$.

In one embodiment the medical multi-layer product has a density in the range of 300-800 $kg/m^3$, such as 350-700 $kg/m^3$, for example 450-650 $kg/m^3$. The density may be measured as apparent bulking density by ISO 534.

The medical multi-layer products may be used in several applications. One specific field is medical applications, wherein the materials are applied on living tissue, such as skin. The structures may be used in medical products, such as patches, dressings, bandages, filters and the like. The medical products may also be therapeutic products, such as therapeutic patches containing medicament. In general a layer comprising nanofibrillar cellulose will be in contact with the skin during the use. A layer of nanofibrillar cellulose may provide advantageous effects when it is in direct contact with the skin, for example it may promote healing of a wound or other damage on a skin, or it may promote delivery of substances from the multi-layer product to the skin.

The term "wound" as used herein refers to any damages, injuries, diseases, disorders or the like on a tissue, such as skin, including open or closed wounds, wherein the healing of the wound is desired and may be promoted with the product described herein. The wound may be clean, contaminated, infected or colonized, wherein especially in the latter cases a therapeutic agent, such as an antibiotic, may be administered. Examples of open wounds include abrasions, avulsions, incisions, lacerations, puncture wounds and penetration wounds. Examples of closed wounds include hematomas, crush injuries, sewn wounds, grafts and any skin conditions, diseases or disorders. Examples of conditions, diseases or disorders of the skin include acne, infections, vesiculobullous diseases, cold sore, cutaneous candidiasis, cellulitis, dermatitis and eczema, herpes, hives, lupus, papulosquamous, urticaria and erythema, psoriasis, rosacea, radiation-related disorders, pigmentation, mucinoses keratosis, ulcer, atrophy, and necrobiosis, vasculitis, vitiligo, warts, neutrophilic and eosinophilic diseases, congenital, neoplasms and cancer, such as melanomas and tumours of epidermis or dermis, or other diseases or disorders of epidermis and dermis.

A medical multi-layer product comprising a therapeutic agent may be provided, wherein the gauze and/or one or more layer(s) comprising nanofibrillar cellulose contain(s) one or more therapeutic agent, such as a medicament or drug. Also the term pharmaceutical agent may be used interchangeably instead of the term therapeutic agent. Such agents are active or effective agents, which are usually present in effective amounts. Such an agent may be provided in a predetermined amount, for example in an amount configured to provide a desired dose of the agent during a certain time period, and/or configured to provide a desired effect on the target, such as skin or other tissue. The content of the therapeutic agent in a layer may be for example in the range of 0.1-5%. Especially if the therapeutic agent is included in a layer comprising nanofibrillar cellulose, a sustained or prolonged release of the agent may be provided. In such case the layer comprising nanofibrillar cellulose may contain a portion of moisture to enable permeability of the agent. The moisture content of a layer comprising nanofibrillar cellulose and therapeutic agent may be in the range of 0-10%, such as in the range of 5-7%. The therapeutic agents may be present in water-soluble form, fat-soluble form or in an emulsion, or in another suitable form.

Examples of therapeutic agents which may be administered by using the medical multi-layer products described herein include antibiotics, pain relievers, such as lidocaine; nicotine; opioids, such as fentanyl or buprenorphine; hormones, such as estrogen, contraceptives or testosterone; nitroglycerin; scopolamine; clonidine; antidepressants, such as selegiline; ADHD medication, such as methylphenidate; vitamins, such as B12 or cyanocobalamin; 5-hydroxytryptophan; Alzheimer's medication, such as rivastigmine; acne medication; antipsoriatics, glucocorticoids such as hydrocortisone; or any other medication for treating diseases or disorders of a skin. Therapeutic agents may be used for example in medical patches, which may be used on healthy skin or on damaged skin, to provide a prolonged, sustained or extended release of the therapeutic agent from the patch, for example during a period of several hours, for up to 6, 12, 24 or even 48 hours.

One embodiment provides the medical multi-layer product comprising antibiotic agent. Such a product is especially suitable for treating wounds, wherein the wound treating properties are combined with antibiotic properties which prevents infections caused by harmful microbes in the wound. Examples of suitable antibiotics include especially topical antibiotics, such as bacitracin, erythromycin, clindamycin, gentamycin, neomycin, polymyxin, mupirocin, tetracycline, meclocycline, (sodium) sulfacetamide, benzoyl peroxide, and azelaic acid, and combinations thereof. Also other types of antibiotics, such as systemic antibiotics, may be provided, for example penicillins, such as phenoxymethylpenicillin, flucloxacillin and amoxicillin; cephalosporins, such as cefaclor, cefadroxil and cephalexin; tetracyclines, such as tetracycline, doxycycline and lymecycline; aminoglycosides, such as gentamicin and tobramycin; macrolides, such as erythromycin, azithromycin and clarithromycin; clindamycin; sulphonamides and trimethoprim; metronidazole and tinidazole; quinolones, such as ciprofloxacin, levofloxacin and norfloxacin.

Antibiotics may be also used for treating acne, for example clindamycin, erythromycin, doxycycline, tetracycline etc. Also other agents may be used, such as benzoyl peroxide, salicylic acid, topical retinoid medicines, such as tretinoin, adapalene or tazarotene, azelaic acid, or androgen blockers such as spirolactone. Psoriasis may be treated for example with steroids, such as corticosteroids, moisturizers, calciprotriene, coal tar, vitamin D, retinoids, tazatorene, anthralin, salisylic acid, methotrexate, or cyclosporine. Insect bites or poison ivy exposure may be treated with agents such as hydrocortisone, emu oil, almond oil, ammonia, bisabolol, papain, diphenylhydramine, jewelweed extract or calamine. Some of these or other treatment agents may be also categorized as cosmetic agents.

One embodiment provides a medical product, such as a dressing, a patch or a filter, comprising the medical multi-layer product described herein.

One embodiment provides the medical multi-layer product for use for treating and/or covering skin wounds or other damages. One embodiment provides such a medical product for use as a dressing or a patch, or in a dressing or a patch, for treating and/or covering skin wounds or other damages.

One embodiment provides such a medical product for use for treating and/or covering skin wounds covered with a graft, such as a skin graft. One embodiment provides such a medical product for use as a dressing or a patch, or in a dressing or a patch, for treating and/or covering skin wounds covered with a graft, such as a skin graft.

A dressing is a sterile pad or compress applied to a wound to promote healing and/or prevent further harm. A dressing is designed to be in direct contact with the wound, as distinguished from a bandage, which is most often used to hold a dressing in place. Some organizations classify them as the same thing (for example, the British Pharmacopoeia) and the terms are used interchangeably by some people. Dressings are frequently used in first aid and nursing.

One embodiment provides the medical multi-layer product for use for administering therapeutic agent. In such case the medical multi-layer product may be provided as such or for example in a patch. One or more therapeutic agent(s) may be included, for example impregnated, in the product as described herein, and the administration to a patient may be dermal or transdermal.

One embodiment provides a cosmetic product, such as a dressing, a mask or a patch, comprising the medical multi-layer product. Such a product may be called also as a cosmetic multi-layer product. The product may be provided in various shapes, for example a mask may be designed to fit onto face, for example below eye or onto chin, nose or forehead. One embodiment provides the medical multi-layer product for use as a cosmetic product. The multi-layer product may be used for releasing one or more cosmetic agent(s) to the user, such as to the skin of the user. Such a cosmetic product may comprise one or more cosmetic agent(s). Cosmetic agent(s) may be included, for example impregnated, in the product, such as into a layer comprising nanofibrillar cellulose, wherefrom they will be released or delivered. The content of a cosmetic agent in a layer may be for example in the range of 0.1-5%. The cosmetic agents may be present or provided in the product similarly as explained above for therapeutic agents, and vice versa. The cosmetic use may be analogous to medical use described herein, especially the administering of therapeutic agent.

Cosmetic agents may be used also for cosmetically treating skin diseases or disorders, such as those mentioned herein. Such cosmetic multi-layer products may be used for example for treating pimples, acneic skin, brown spots, wrinkles, oily skin, dry skin, aged skin, spider veins, after sun erythemas, black circles etc. Examples of cosmetic patches include skin cleansers, such as pore cleansers, blackhead removers, stretching stripes, short-term patch-like masks, short-term treatment patches and overnight treatment patches.

Examples of cosmetic agents include forms of vitamins and precursors thereof, such as vitamin A; for example retinoids, such as retinaldehyde (retinal), retinoic acid, retinyl palmitate and retinyl retinoate, ascorbic acid, alpha-hydroxy acids such as glycolic acid and lactic acid; glycols; biotechnology products; keratolytics; amino acids; antimicrobials; moisturizers; pigments; antioxidants; plant extracts; cleansing agents or make-up removers; anti-cellulite agents such as caffeine, carnitine, Ginkgo biloba and horse-chestnut; conditioners; fragrances such as aromatherapy agents and perfumes; humectants such as urea, hyaluronic acid, lactic acid and glycerine; emollients such as lanolin, triglycerides and fatty acid esters; FR scavengers, singlet oxygen scavengers, superoxide scavengers or hydrogen peroxide scavengers, such as ascorbic acid (vitamin C), glutathione, tocopherol (vitamin E), carotenoids, coenzyme Q10, bilirubin, lipoic acid, uric acid, enzyme mimetic agents, idebenone, polyphenols, selenium, spin traps such as phenyl butyl nitrone (PBN), protein methionine groups, superoxide dismutase, catalase, selenium peroxidases, heme oxygenases etc. or combinations thereof. The cosmetic agents may be present in water-soluble form, fat-soluble form or in an emulsion, or in another suitable form.

One embodiment provides a method for cosmetically treating skin, the method comprising applying the medical multi-layer product or the medical product described herein onto skin.

The products containing effective or active agents, such as therapeutical or cosmetic agents, may contain one or more layers of nanofibrillar cellulose. The agent may be contained in one layer only, or it may be contained in two or more layers. Two or more layers may also contain a different agent in each layer. Two or more different agents may be all therapeutic agents or they may be all cosmetic agents or they may comprise both therapeutic and cosmetic agents, for example a first therapeutic agent in a first layer and a second therapeutic agent in a second layer, or a therapeutic agent in a first layer and a cosmetic agent in a second layer. Further, a first layer containing no such agent may be provided, which layer is to be applied against the skin, and a second layer next to the first layer or at the other side of the gauze may contain the agent. Alternatively, the first layer may contain the agent and the second layer next to the first layer or at the other side of the gauze does not contain any agents. With such arrangements it is possible to control for example the delivery rate or order of the agents.

A "patch" as used herein refers to a medical or cosmetic product which may be applied onto skin. Examples of patches include dermal patch and transdermal patch. A dermal patch or skin patch is a medicated adhesive patch that is placed on the skin to deliver a medication into the skin. A transdermal patch is a medicated adhesive patch that is applied on the skin to deliver a specific dose of medication through the skin and into the bloodstream. In one example this promotes healing to an injured area of the body. A patch may contain a release liner, which protects the patch during storage and is removed prior to use, and/or adhesive for adhering the patch to the skin, and/or backing for protecting the patch from the outer environment. Examples of release liners include paper-based liners, such as glassine paper, densified Kraft super-calendered paper, clay-coated paper, silicone-coated paper and polyolefine-coated paper; plastic based liner, such as polystyrene, polyester, polyethylene, cast polypropylene and polyvinyl chloride; and composite material liners based on the combination of several films. Adhesive layers may contain for example pressure sensitive adhesive (PSA).

Figure 2:
FIG. 2 shows an example of a final medical multi-layer product packed in a single packing.

One embodiment provides the medical multi-layer product or the medical product described herein packed in a separate packing. Separate packings may be provided as a series of packings. Usually such packed products are provided as sterilized. FIG. 2 shows an example of the medical multi-layer product packed in a sterile packing.

One embodiment provides a kit comprising the medical multi-layer product, the medical product or the cosmetic product described herein, for example a packed multi-layer product, wherein the kit may contain one or more of the packed multi-layer products. The kit may also contain other materials or equipment, such as a container containing saline solution or the like for pretreating the product(s) prior to use.

One embodiment provides a method for treating skin wounds or other damages or injuries, the method comprising applying the medical multi-layer product or the medical product described herein onto the wound, damage, or injury. One specific embodiment provides a method for treating skin wounds covered with a graft, such as a skin graft, for example a mesh graft or a full thickness graft, the method comprising applying the medical multi-layer product or the medical product described herein onto the graft.

Grafting refers to a surgical procedure to move tissue from one site to another on the body, or from another person, without bringing its own blood supply with it. Instead, a new blood supply grows in after it is placed. Autografts and isografts are usually not considered as foreign and, therefore, do not elicit rejection. Allografts and xenografts are recognized as foreign by the recipient and are rejected.

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance. There are two types of skin grafts: Split-thickness skin grafts (epidermis+part of the dermis) and full-thickness skin grafts (epidermis+entire thickness of the dermis).

A mesh graft is a full- or partial-thickness sheet of skin that has been fenestrated to allow drainage and expansion. Mesh grafts are useful in many locations on the body because they conform to uneven surfaces. They can be placed in locations that have excessive motion because they can be sutured to the underlying wound bed. Additionally, their fenestrations provide outlets for fluid that may accumulate beneath the graft, which helps reduce tension and the risk of infection and improve vascularization of the graft.

It was found out in the clinical tests that the multi-layered product attaches to a graft area and acts as a protective layer. As the graft heals, the product forms a scab-like structure together with the graft. The properties of the multi-layer product comprising nanofibrillar cellulose promote the healing, and the membrane with the formed dry scab will come loose in similar way as a regular scab behaves in normal wound healing process.

Before applying the medical multi-layer product onto skin the product may be pretreated i.e. moisture or wetted, in general with an aqueous solution. The moisturizing or wetting may be carried out for example by using water or regular physiological saline solution, which is usually a solution of 0.90% w/w of NaCl, having an osmolality of about 308 mOsm/l. Other types of aqueous solutions may also be used, such as saline solutions with different concentrations. Moisturizing or wetting the material enhances contact with the skin and the moldability of a sheet of material.

EXAMPLES

Example 1

Membranes were prepared for wound healing applications from non-modified nanofibrillar cellulose manufactured from wood cellulose. The nanofibrillar cellulose was diluted to a concentration of 0.3% to form a furnish and drained in a modified Büchner funnel with extra fine forming fabric. The membrane were formed by press drying at high temperature. Basic weight of the obtained membranes was approximately 55 g/m$^2$.

In the tests different amounts of beaten chemical pulp were added to the furnish. A significant difference in drainage time was noticed when chemical pulp fibers were introduced to furnish (Table 1). Only 1% share of chemical pulp was able to speed up the drainage by over 50%. No further drainage was seen with higher chemical pulp additions levels within the tested range. The drainage time was measures as an average of 4-5 membranes.

TABLE 1

| Trial point | Furnish composition | Drainage time (min) |
|---|---|---|
| 1 | 100% NFC | 8.3 |
| 2 | 99% NFC/1% pulp | 3.7 |
| 3 | 97% NFC/3% pulp | 3.8 |
| 4 | 95% NFC/5% pulp | 3.7 |
| 5 | 90% NFC/10% pulp | 3.9 |

The effect of chemical pulp fibers can be seen in membrane thickness (Table 2). Also a significant increase in tear strength was seen.

TABLE 2

| | Air conditioned | | | | |
|---|---|---|---|---|---|
| Trial points | Drainage time/min | Grammage g/m$^2$ | Thickness, avr/μm | Tear avr/mN | Tear index, avr/ mNm$^2$/g |
| Standard 100% NFC, 26-29 | 6.6 | 52.8 | 50.6 | 41.67 | 0.79 |
| 95% NFC/5% chemical pulp, 30-32 | 5.5 | 52.9 | 53.4 | 111.33 | 2.11 |

Example 2

Different membranes were tested for their properties. Non-modified nanofibrillar cellulose was manufactured from wood cellulose. Table 3 shows results from the tests wherein membranes containing 100% of nanofibrillar cellulose, 95% of nanofibrillar cellulose and 5% of softwood pulp, and 45% of nanofibrillar cellulose and 55% of softwood pulp (trial points 26-33) were tested. Table 1 also shows properties of different 100% nanofibrillar membranes layered with a gauze (M1-M10 and N1-N10), wherein the gauze portion is always the same but the amount of nanofibrillar cellulose is different. The gauze was non-woven viscose-polyester gauze sold with trade name Mesoft.

TABLE 3

| Trial points | NFC | Chem. pulp | NFC/% | Chem. pulp/% | Gauze | Drainage time/min | Grammage g/m$^2$ Air conditioned | Thickness, avr/μm Air conditioned | Density/ g/cm$^3$ |
|---|---|---|---|---|---|---|---|---|---|
| 26-29 | N | SW | 100 | 0 | No | 6.6 | 52.8 | 50.6 | 1044 |
| 30-32 | N | SW | 95 | 5 | No | 5.5 | 52.9 | 53.4 | 990 |
| 33 | N | SW | 45 | 55 | No | 2.5 | 58.6 | 90.9 | 645 |
| M1-M4 | G | | 100 | 0 | Yes | 16.3 | 86.3 | 134.1 | 643 |
| M5-M7 | G | | 100 | 0 | Yes | 8.3 | 73.4 | 125.8 | 584 |
| M8-M9 | G | | 100 | 0 | Yes | 6.0 | 62.8 | 120.3 | 522 |
| M10 | G | | 100 | 0 | Yes | 4.0 | 53.8 | 118.4 | 454 |
| N1-N2 | G | | 100 | 0 | Yes | 16.5 | 83.3 | 131.3 | 634 |
| N3-N10 | G | | 100 | 0 | Yes | 8.4 | 73.7 | 124.0 | 595 |

Example 3

Three-layer structures were prepared having a first layer comprising non-modified nanofibrillar cellulose, a non-woven viscose-polyester gauze in the middle, and a second layer comprising non-modified nanofibrillar cellulose on the top. Non-modified nanofibrillar cellulose was manufactured from wood cellulose. The gauze was non-woven viscose-polyester gauze sold with trade name Mesoft.

The samples were air conditioned having a moisture content of about 6%. Properties such as tear index, break elongation, tensile index, tear strength and tensile strength were measured for different samples. Tear index was determined by ISO 1974. The break elongation may be determined as stretch at break by ISO 1924-3. Tensile index and tensile strength were determined with ISO 1924-3. The gauze had a main direction of fibers in the longitudinal direction of a sheet, which direction could be detected visually, and is herein called as "machine direction" (md). There were problems when measuring the tear properties of the gauze in cross direction because of the strong elongation of the gauze alone in the cross direction.

Samples V1-V4 had a grammage of 74.1 g/m$^2$. Samples W2, W3, X1, and X3 had a grammage of 64.4 g/m$^2$. The gauze had a grammage of 32.5 g/m$^2$ and original thickness of about 150 μm. Grammages were determined by ISO 536. The gauze was pretreated before the measurements by wetting and drying to remove folds in the gauze sheet, which probably led to decreased average thickness of about 105 μm. The density of the gauze was 307 g/cm$^3$.

Properties of the three-layer structures were compared with the gauze alone (Table 4); md=machine direction, cd=cross (transverse) direction.

TABLE 4

| Sample | Tear index md mNm²/g | Tear index cd mNm²/g | Break elong md % | Break elong cd % | Tensile index md Nm/g | Tensile index cd Nm/g | Tear str. md mN | Tear str. cd mN | Tensile strength md kN/m | Tensile strength cd kN/m |
|---|---|---|---|---|---|---|---|---|---|---|
| V1-V4 | 18.7 | 64.9 | 1.6 | 1.4 | 48.4 | 34.7 | 1382 | 4805 | 3.6 | 2.6 |
| W2, W3, X1, X3 | 23.0 | 43.7 | 2.0 | 1.9 | 49.6 | 33.6 | 1481 | 2811 | 3.2 | 2.2 |
| Gauze | 55.2 | | 13.8 | | 35.2 | | 1794 | | 1.1 | |

Example 4

Multi-layer products corresponding to the products described in Example 3 were tested in a clinical trial for their wound healing properties in skin graft donor site treatment for 10 patients having skin burns. The multi-layer products were moisturized with physiological saline solution. The skin draft donor sites were covered with the multi-layer products after hemostasis. The multi-layer products dehydrated gradually and attached to the donor site. The multi-layer products were compared to commercial lactocapromer membranes, and it was discovered that in some cases the multi-layer products were better than the commercial products. For example the healing rate, which was determined by the detachment of the material from the wound, was very good for the multi-layer products and healthy epithelialized skin was revealed under the detached membrane. The multi-layer products attached to wound bottom and remained until the graft site had renewed. The patient showed no allergic reaction or inflammatory response to the multi-layer products.

The invention claimed is:

1. A medical multi-layer product comprising
   a first layer comprising plant nanofibrillar cellulose having a moisture content in the range of 0-10% (w/w), and
   a layer of gauze;
   wherein the product has a tear index in the range of 18-100 mNm²/q.
2. The medical multi-layer product of claim 1, wherein the first layer comprising plant nanofibrillar cellulose has a moisture content in the range of 5-7% (w/w).
3. The medical multi-layer product of claim 1, comprising a second layer comprising nanofibrillar cellulose.
4. The medical multi-layer product of claim 3, wherein the plant nanofibrillar cellulose in the first layer and/or in the second layer, when dispersed in water, provides a Brookfield viscosity of at least 2000 mPa·s, measured at a consistency of 0.8% (w/w) and at 10 rpm.
5. The medical multi-layer product of claim 1, wherein the gauze comprises natural gauze.
6. The medical multi-layer product of claim 1, wherein the gauze comprises synthetic gauze or semi-synthetic.
7. The medical multi-layer product of claim 1, wherein the plant nanofibrillar cellulose comprises non-modified nanofibrillar cellulose.
8. The medical multi-layer product of claim 1, wherein the plant nanofibrillar cellulose comprises chemically modified plant nanofibrillar cellulose.
9. The medical multi-layer product of claim 1, wherein a layer of plant nanofibrillar cellulose has a thickness in the range of 5-60 μm.
10. The medical multi-layer product of claim 1, having a thickness in the range of 100-500 μm.
11. The medical multi-layer product of claim 1, wherein the first layer comprising t nanofibrillar cellulose comprises an amount of non-nanofibrillar pulp in the range of 0.1-60% (w/w) of total cellulose in said layer.
12. The medical multi-layer product of claim 1, wherein product has a grammage in the range of 50-100 g/m².
13. The medical multi-layer product of claim 1 wherein the product has a density in the range of 300-800 kg/m³.
14. The medical multi-layer product of claim 1, wherein the plant nanofibrillar cellulose in the first layer has a number average diameter of a fibril in the range of 1-100 nanometers.
15. The medical multi-layer product of claim 1 comprising a therapeutic agent.
16. The medical multi-layer product of claim 1 comprising a cosmetic agent.
17. A medical product comprising the medical multi-layer product of claim 1.
18. A method for treating skin wounds or other damages or injuries, the method comprising applying the medical multi-layer product of claim 1 onto the wound, damage, or injury.
19. A method for treating skin wounds covered with a graft the method comprising applying the medical multi-layer product of claim 1 onto the graft.
20. A method for administering therapeutic agent, the method comprising applying the medical multi-layer product of claim 15 onto skin.
21. A method for preparing a medical multi-layer product, the method comprising
   providing a filter,
   providing a dispersion comprising plant nanofibrillar cellulose,
   providing a gauze,
   applying the dispersion onto the filter,
   applying the gauze onto the dispersion to form a structure, and
   dewatering the structure through the filter to obtain the medical multi-layer product comprising a first layer comprising plant nanofibrillar cellulose having a moisture content in the range of 0-10% (w/w).
22. The method of claim 21, further comprising providing a second dispersion comprising nanofibrillar cellulose and applying the second dispersion comprising nanofibrillar cellulose onto the gauze.
23. A medical multi-layer product comprising
   a first layer comprising plant nanofibrillar cellulose having a moisture content in the range of 0-10% (w/w), and
   a layer of gauze;
   wherein the product has a tear index in the range of 18-100 mNm²/g, and
   wherein the product is obtained with the method of claim 21.

24. A method for preparing a medical multi-layer product, the method comprising
- providing a first layer comprising plant nanofibrillar cellulose having a moisture content in the range of 0-10% (w/w),
- providing a layer of gauze, and
- laminating the first layer comprising plant nanofibrillar cellulose and the layer of gauze to obtain the medical multi-layer product;
- wherein the product has a tear index in the range of 18-100 mNm$^2$/q.

25. The method of claim 24, wherein the first layer comprising plant nanofibrillar cellulose has a moisture content in the range of 1-10%.

26. The method of claim 24, wherein the gauze comprises natural gauze.

27. The method of claim 24, wherein the gauze comprises synthetic gauze or semi-synthetic.

28. The method of claim 24, wherein the plant nanofibrillar cellulose in the first layer comprising plant nanofibrillar cellulose when dispersed in water, provides a Brookfield viscosity of at least 2000 mPa·s, measured at a consistency of 0.8% (w/w) and at 10 rpm.

29. The method of claim 24, wherein the first layer comprising plant nanofibrillar cellulose comprises non-modified plant nanofibrillar cellulose.

30. The method of claim 24, wherein the first layer comprising plant nanofibrillar cellulose comprises chemically modified plant nanofibrillar cellulose.

31. The method of claim 24, wherein the first layer comprising plant nanofibrillar cellulose comprises an amount of non-nanofibrillar pulp in the range of 0.1-60% (w/w) of total cellulose in said layer.

32. The method of claim 24, comprising providing a therapeutic agent and including the therapeutic agent to the first layer comprising plant nanofibrillar cellulose.

33. The method of claim 24, comprising providing a cosmetic agent and including the cosmetic agent to the first layer comprising plant nanofibrillar cellulose.

* * * * *